United States Patent
Eberhard et al.

(10) Patent No.: US 7,084,089 B2
(45) Date of Patent: Aug. 1, 2006

(54) PROCESS FOR THE CARBONYLATION OF ETHYLENICALLY UNSATURATED COMPOUNDS, BIDENTATE DIPHOSPHINE COMPOSITION USED IN THIS PROCESS AND A PROCESS FOR PREPARATION OF THIS BIDENTATE DIPHOSPHINE COMPOSITION

(75) Inventors: Michael Rolf Eberhard, Bristol (GB); Paul Gerard Pringle, Bristol (GB)

(73) Assignee: Shell Oil Company, Houston, TX (US)

( * ) Notice: Subject to any disclaimer, the term of this patent is extended or adjusted under 35 U.S.C. 154(b) by 12 days.

(21) Appl. No.: 10/210,347

(22) Filed: Jul. 31, 2002

(65) Prior Publication Data

US 2004/0024258 A1 Feb. 5, 2004

(51) Int. Cl.
*B01J 31/00* (2006.01)
(52) U.S. Cl. ..................... 502/162; 568/429
(58) Field of Classification Search .......... 252/181.11, 252/181.21, 182.3; 568/12, 429; 502/162; 556/21, 18
See application file for complete search history.

(56) References Cited

U.S. PATENT DOCUMENTS

| | | | |
|---|---|---|---|
| 3,527,818 A | 9/1970 | Mason et al. | 260/632 |
| 4,163,760 A | 8/1979 | Elsner et al. | 260/606.5 |
| 5,218,086 A * | 6/1993 | Van Doorn et al. | 528/392 |
| 5,256,827 A * | 10/1993 | Slaugh et al. | 568/454 |
| 5,304,686 A | 4/1994 | Slaugh et al. | 568/496 |
| 5,488,174 A * | 1/1996 | Drent et al. | 568/464 |
| 5,811,590 A | 9/1998 | Arnoldy et al. | 568/451 |
| 6,037,500 A | 3/2000 | Zhang | 568/12 |
| 6,080,898 A | 6/2000 | Drent et al. | 568/861 |
| 6,348,612 B1 * | 2/2002 | Burkart et al. | 558/157 |
| 6,492,544 B1 * | 12/2002 | Krimmer et al. | 560/170 |
| 2002/0016484 A1 | 2/2002 | Drent et al. | 556/70 |

FOREIGN PATENT DOCUMENTS

| | | |
|---|---|---|
| EP | 0495547 A2 | 1/1992 |
| EP | 0529698 A2 | 7/1992 |
| EP | 0872482 A2 | 4/1998 |
| EP | 0 864 576 A1 * | 9/1998 |
| EP | 0864576 A1 | 9/1998 |
| GB | 1127965 | 9/1968 |
| GB | 2306344 A | 5/1997 |
| WO | WO 95/05354 | 2/1995 |
| WO | WO 97/003943 | 2/1997 |
| WO | WO 00/02375 | 1/2000 |
| WO | WO 00/52017 | 9/2000 |
| WO | WO 00/56695 | 9/2000 |
| WO | WO 01/87899 A1 | 11/2001 |

OTHER PUBLICATIONS

"A Simple Procedure for the Separation of the Catalytically Important Phosphabicyclononane Isomers," by J. H. Downing et al., published in Chemical Communications, 1997, pp. 1527-1528.
Elsner et al. (Chem. Abstr. 1978, vol. 89, 180154x).
"New Strategies in 9-Phosphabicyclononane Chemistry," by Michael R. Eberhard, A thesis submitted to the University of Bristol in accordance with the requirements for the degree of Doctor of Philisophy in the School of Chemistry, Faculty of Science, Jan. 2001.
"New Strategies in 9-Phosphabicyclononane Chemistry," Michael R. Eberhard, A thesiss submitted to the University of Bristol in accordance with the requirements for the degree of Doctor of Philosophy in the School of Chemistry, Faculty of Science, Jan. 2001.

* cited by examiner

*Primary Examiner*—Johann Richter
*Assistant Examiner*—Chukwuma Nwaonicha

(57) ABSTRACT

Process for the carbonylation of optionally substituted ethylenically unsaturated compounds by reaction with carbon monoxide and a coreactant in the presence of a catalyst system. The catalyst system includes
(a) a source of Pt group metal cations,
(b) a certain bidentate diphosphine composition.

In addition a method to prepare such a bidentate diphosphine composition is described.

9 Claims, No Drawings

PROCESS FOR THE CARBONYLATION OF ETHYLENICALLY UNSATURATED COMPOUNDS, BIDENTATE DIPHOSPHINE COMPOSITION USED IN THIS PROCESS AND A PROCESS FOR PREPARATION OF THIS BIDENTATE DIPHOSPHINE COMPOSITION

The present invention relates to a process for the carbonylation of optionally substituted ethylenically unsaturated compounds by reaction with carbon monoxide and a coreactant in the presence of a certain catalyst system.

BACKGROUND OF THE INVENTION

A commercially important carbonylation reaction, using hydrogen as coreactant, is the hydroformylation of olefins, which are reacted with carbon monoxide and hydrogen to form aldehydes and/or alcohols having one carbon atom more than the precursor olefin. Depending on catalyst, reaction conditions and substrates, the hydroformylation can proceed with varying selectivities to the several possible isomeric aldehydes or alcohols in varying yields, as side reactions occur to a smaller or larger extent. Generally only one isomeric product is preferred. For many applications the presence of branched aldehydes or alcohols is undesirable. Moreover, in view of biological degradability, it is considered advantageous to obtain products having a high content of the linear isomer. The selectivity towards one of several possible isomeric products is called regioselectivity. For hydroformylation a regioselectivity towards reaction at the primary carbon atom, resulting in a linear product, is desirable.

WO-A-95/05354 describes the carbonylation of ethylenically unsaturated compounds by reaction with carbon monoxide and hydrogen, i.e. hydroformylation, in the presence of a catalyst system comprising a Group VIII metal cation, viz. cationic palladium and platinum, and a bidentate ligand, viz. a diphosphine. In the examples amongst others 1,2-bis (1,4-cyclooctylene phosphino)ethane, i.e. in IUPAC nomenclature 1,2-PP'bis(9-phosphabicyclo[4.2.1]nonyl)ethane; 1,3-bis(1,4-cyclooctylene phosphino)propane, i.e. in IUPAC nomenclature 1,3-PP'bis(9-phosphabicyclo[4.2.1]nonyl) propane; and 1,2-bis(2,6-dimethyl, 1,4-cyclooctylene phosphino)ethane, i.e. in IUPAC nomenclature 1,2-PP'bis(2,6-dimethyl, 9-phosphabicyclo[4.2.1]nonyl)ethane are used as bidentate diphosphine ligands. The phosphabicyclononyl groups in these ligands are all substituted or non-substituted 1,4-cyclooctylenephosphino groups, i.e. in IUPEC nomenclature 9-phosphabicyclo[4.2.1]nonyl groups. Such a 9-phosphabicyclo[4.2.1]nonyl group is visualised in Figure A.

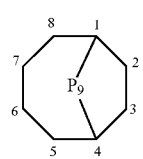

FIG. A

As is illustrated by the examples the hydro-formylation of ethylenically unsaturated compounds with a catalyst system containing these diphosphines results in acceptable selectivities towards the linear product.

The 9-phosphabicyclo[4.2.1]nonyl group visualized in Figure A is an example of an asymmetrical phosphabicycloalkyl group. In an asymmetrical phosphabicycloalkyl group the bridges not containing the phosphorus atom have an unequal number of atoms in the bridge. By a symmetrical phosphabicycloalkyl group is understood that the bridges (i.e. the hydrocarbyl groups connecting the tertiary carbon atoms), which do not contain the phosphorus atom, have an equal number of atoms. An example of such a symmetrical group is the 9-phosphabicyclo[3.3.1]nonyl group which is visualised in Figure B.

FIG. B

WO-A-00/02375 describes a method to prepare a phosphorus-containing ligand by refluxing a phosphabicyclononane hydride with 1,2-dibromoethane in acetonitrile. After neutralisation with sodium hydroxide a bis-(9-phosphabicyclononyl)ethane can be isolated. The phosphabicyclononane hydride can conveniently be prepared as described by Elsner et al. (Chem. Abstr. 1978, vol. 89, 180154x).

In addition, non-pre-published WO-A-01/87899 describes the preparation of a bidentate diphosphine ligand by reacting P-cyclo-octyl hydride (e.g. phosphabicyclononane hydride) and butyllithium to generate a lithium cyclo-octyl phosphide and subsequently reacting with an appropriate substituted or non-substituted alkane diol sulphate ester. The P-cyclooctyl hydride can conveniently be prepared as described by Elsner et al. (Chem. Abstr. 1978, vol. 89, 180154x).

In their article entitled "A simple procedure for the separation of the catalytically important phobane isomers", published in Chemical Communications, 1997, pages 1527–1528, J. H. Downing et al. indicate that to that date there had been no reports of the separation of the symmetrical and asymmetrical isomers of phosphabicyclononanes, although, by exploiting the difference in reactivity between the isomers, ligands derived from the symmetrical isomer had been isolated.

In the article of J. H. Downing et al. a laborious method is provided for separation of the isomers of phosphabicyclononane. The method comprises:

a) reacting a mixture of both symmetrical and asymmetrical phosphabicyclononane hydride with formaldehyde ($CH_2O$) in the presence of hydrochloric acid (HCl), yielding phosphonium salts;

b) reacting these phosphonium salts with sodium hydroxide (NaOH), yielding a charged symmetrical phosphine and a neutral asymmetrical phosphine;

c) extracting the neutral asymmetrical phosphine with pentane, leaving relatively pure, charged symmetrical phosphine in an aqueous solution;

d) treating the aqueous solution with sodium hydroxide to obtain the neutral symmetrical phosphine.

The symmetrical phosphabicyclononane is used in the synthesis of 1,3-PP'bis(9-phosphabicyclo[3.3.1]nonyl) propane. The overall yield of this preparation was only 17%.

The article does not describe the preparation of any other bidentate diphosphine having general formula I.

Although good results with regard to the regioselectivity towards a linear product are obtained in WO-A-95/05354, there is room for further improvement.

It is therefore desirable to provide a process for the carbonylation of ethylenically unsaturated compounds by reaction with carbon monoxide and a coreactant, which results in an improved regioselectivity towards a linear product.

SUMMARY OF THE INVENTION

A process for the carbonylation of optionally substituted ethylenically unsaturated compounds is provided, by reaction with carbon monoxide and a coreactant in the presence of a catalyst system including:

(a) a source of Pt group metal cations, (b) a bidentate diphosphine composition wherein more than 60% w/w of bidentate diphosphine present in the bidentate diphosphine composition has the general formula II $$X^1—R—X^2 \quad (II)$$

wherein $X^1$ and $X^2$ independently represent an optionally substituted symmetrical phosphabicycloalkyl group, having at least 5 ring atoms; and R represents a bivalent organic bridging group, connecting both phosphorus atoms. The catalyst composition is also provided.

A process for the separation of symmetrical phosphabicycloalkane from a composition containing symmetrical and asymmetrical phosphabicycloalkanes is also provided, comprising:

a) adding a source to protonate a phosphabicycloalkane to a composition containing symmetrical phosphabicycloalkane (SPBA) and asymmetrical phosphabicycloalkane (APBA), thereby providing a composition comprising protonated symmetrical phosphabicycloalkane (SPBA+) and non-protonated asymmetrical phosphabicycloalkane (APBA);

b) separating protonated symmetrical phosphabicycloalkane (SPBA+) and non-protonated asymmetrical phosphabicycloalkane (APBA), thereby providing separated protonated symmetrical phosphabicycloalkane (SPBA+) and separated non-protonated asymmetrical phosphabicycloalkane (APBA); and c) adding a source to de-protonate the separated protonated symmetrical phosphabicycloalkane (SPBA+), thereby providing separated non-protonated symmetrical phosphabicycloalkane (SPBA).

Another process for the separation of symmetrical phosphabicylcoalkane from a composition containing symmetrical and asymmetrical phosphabicycloalkanes is provided, comprising:

i) dissolving a composition comprising symmetrical phosphabicycloalkane (SPBA) and non-protonated asymmetrical phosphabicycloalkane (APBA) in a non-water miscible solvent, which does not dissolve protonated symmetrical phaosphabicycloalkane (SPBA+), thereby providing a non-aqueous phosphabicycloalkane (PBA) solution;

ii) combining the non-aqueous PBA solution with an aqueous solution of an acid, thereby providing an aqueous phase containing SPBA+and a non-aqueous phase containing APBA;

iii) separating the aqueous phase containing SPBA+and the non-aqueous phase containing APBA, thereby providing an aqueous solution containing SPBA+and a non-aqueous solution containing APBA;

iv) combining the aqueous solution containing SPBA+with a non-water miscible solvent and an aqueous solution of a base, thereby providing a non-aqueous solution containing SPBA; and v) removing the solvent from the non-aqueous solution containing SPBA, thereby producing separated SPBA.

DETAILED DESCRIPTION OF THE INVENTION

It has now surprisingly been found that when a process for the carbonylation of ethylenically unsaturated compounds is characterised by a Pt group metal based catalyst comprising a specific bidentate diphosphine composition wherein a certain amount of bidentate diphosphine with two symmetrical phosphabicycloalkyl groups is present, unexpected advantages with regard to the regioselectivity towards a linear product are obtained.

The present invention relates to a process for the carbonylation of optionally substituted ethylenically unsaturated compounds by reaction with carbon monoxide and a coreactant in the presence of a catalyst system comprising a source of Pt group metal cations and a bidentate diphosphine having the general formula I $$Q^1\text{-}Z\text{-}Q^2 \quad (I)$$

wherein $Q^1$ and $Q^2$ represent a phosphabicycloalkyl group, having at least 5 ring atoms; and Z represents a bivalent organic bridging group connecting both phosphorus atoms. The present invention in particular relates to such a reaction in which the coreactant is hydrogen.

Accordingly the present invention provides a process for the carbonylation of optionally substituted ethylenically unsaturated compounds by reaction with carbon monoxide and a coreactant in the presence of a catalyst system including:

(a) a source of Pt group metal cations, (b) a bidentate diphosphine composition wherein more than 60% w/w of bidentate diphosphine present in the bidentate diphosphine composition has the general formula II $$X^1—R—X^2 \quad (II)$$

wherein $X^1$ and $X^2$ independently represent an optionally substituted symmetrical phosphabicycloalkyl group, having at least 5 ring atoms; and R represents a bivalent organic bridging group, connecting both phosphorus atoms.

The article of J. H. Downing et al. does not indicate any use, nor any expected advantage, for the 1,3-PP'bis(9-phosphabicyclo[3.3.1]nonyl) propane prepared. On the contrary, by means of reference 5, referring to WO-A-95/05354, the article even indicates a preference for the asymmetrical phosphabicyclononyls.

As will be shown in the examples, however, the use of derivatives of symmetrical phosphabicycloalkane groups is very advantageous for the linearity of the product.

In the general formula II for component b) of the catalyst system, R preferably represents a bivalent organic bridging group containing from 1 to 10, preferably from 2 to 6, more preferably from 2 to 4, and most preferably 2 to 3 atoms in the shortest connection between both phosphorus atoms. Especially preferred is a bivalent organic bridging group having 2 atoms in this connection. Preferably, the bridging group R represents an alkylene group, but it can also comprise a carbon chain, interrupted by one or more hetero atoms, such as nitrogen, sulphur, silicon or oxygen atom. Preferably the shortest connection between both phosphorus atoms contains 2 or 3 carbon atoms, most preferably 2 carbon atoms.

The shortest connection between both phosphorus atoms can be substituted or non-substituted or can form part of a aliphatic or aromatic ring structure. In a preferred embodiment the connection forms part of an optionally substituted saturated or non-saturated aliphatic ring structure, such as for example a substituted or non-substituted cyclopentane, cyclopentene, cyclohexane or cyclohexene. The cycloaliphatic ring can be interrupted by one or more heteroatoms such as nitrogen, sulphur, silicon or oxygen atoms. The aliphatic ring structure can further be substituted with any kind of substituent, including heteroatoms, alkyl groups, cycloalkyl groups and aryl groups. If the connection forms part of an optionally substituted saturated or non-saturated aliphatic ring structure the phosphorus atoms are preferably attached at adjacent positions, for example positions 1 and 2.

More preferably the connection is an ethylene or trimethylene group. Most preferably the connection is a ethylene group. The connection can be a substituted alkylene group with at least one substituent and preferably at least two substituents. If the connection is substituted it is preferably substituted with two to four substituents, more preferably with two to three substituents, and most preferably with two substituents.

The substituents can be attached to any part of the connection. In an advantageous embodiment, the carbon atoms of the connection, which are connected to the phosphorus atoms, are substituted. In this case the bidentate diphosphine has two chiral C-atoms and can have the RR, SS, or R,S meso-form. The R,S meso-form is preferred.

The substituents can contain carbon atoms and/or hetero atoms. Substituents which can be used include groups containing hetero-atoms such as halides, sulphur, phosphorus, oxygen and nitrogen. Examples of such groups include chloride, bromide, iodide, thiol, and groups of the general formula H—O—, $A^1$-O—, —S-$A^1$, —CO-$A^1$, —NH$_2$, —NH$A^1$, —N$A^1A^2$, —CO—N$A^1A^2$, —OH, —PO$_4$, —NO$_2$, —NOH, —CO, —SO$_2$, —SOH, in which $A^1$ and $A^2$, independently, represent aliphatic groups, preferably having from 1 to 10 carbon atoms, more preferably having from 1 to 4 carbon atoms, like methyl, ethyl, propyl and isopropyl.

Preferably the substituents are hydrocarbyl groups. The hydrocarbyl groups themselves can be aromatic, aliphatic or cycloaliphatic. The hydrocarbyl groups can contain carbon atoms and hetero atoms. Hydrocarbyl groups can further include groups containing heteroatoms such as the ones mentioned hereinabove. The hydrocarbyl groups can be straight-chain or branched, and can contain saturated and/or non-saturated links.

Aromatic hydrocarbyl substituent groups can be aryl groups such as phenyl groups and alkyl phenyl groups.

Preferred hydrocarbyl substituent groups are alkyl groups, preferably having from 1 to 10 carbon atoms, more preferably from 1 to 4 carbon atoms. Linear, branched or cyclic alkyl groups can be used. Alkyl groups can be methyl, ethyl, propyl, iso-propyl, butyl and iso-butyl. More preferably methyl groups are used.

Most preferably the bivalent bridging group R is an ethylene group which is di-substituted, preferably with two alkyl groups, most preferably with two methyl groups.

$X^1$ and $X^2$ independently represent a substituted or non-substituted symmetrical phosphabicycloalkyl group. Of the three bridges present in such a phosphabicycloalkyl group, the bridge containing the phosphorus atom is preferably the shortest one. As explained above, the other two bridges have an equal length, i.e. contain an equal number of atoms in the bridge. By "a bridge" is meant a connection between both tertiary carbon atoms.

Preferred are symmetrical phosphabicycloalkyl groups with at least 7 ring atoms (of which one is, of course, a phosphorus atom) and preferably with from 7 to 11 ring atoms. More preferably $X^1$ and $X^2$ represent a substituted or non-substituted symmetrical phosphabicyclononyl group.

Examples of symmetrical phosphabicycloalkyl groups therefore include substituted or non-substituted 2-phosphabicyclo[1.1.1]pentyl; 2-phosphabicyclo[2.1.1]-hexyl; 2-phosphabicyclo[3.1.1]heptyl; 3-phosphabicyclo[3.1.1]heptyl; 7-phosphabicyclo[2.2.1]heptyl; 2-phosphabicyclo[2.2.2]octyl; 2-phosphabicyclo[5.1.1]-nonyl; 3-phosphabicyclo[5.1.1]nonyl; 4-phosphabicyclo[5.1.1]nonyl; 2-phosphabicyclo[3.2.2]nonyl; 3-phosphabicyclo[3.2.2]nonyl; 9-phosphabicyclo[3.3.1]nonyl; 9-phosphabicyclo[3.3.2]decyl; 2-phosphabicyclo[3.3.3]undecyl; 3-phosphabicyclo [3.3.3] undecyl. Of these, substituted or non-substituted 7-phosphabicyclo[2.2.1]heptyl; 9-phosphabicyclo[3.3.1]nonyl; 9-phosphabicyclo[3.3.2]decyl are preferred. Particularly preferred are substituted or non-substituted 9-phosphabicyclo[3.3.1]nonyl groups.

$X^1$ and $X^2$ can each represent a different symmetrical phosphabicycloalkyl or can both represent the same phosphabicycloalkyl. Preferably both $X^1$ and $X^2$ represent the same symmetrical phosphabicycloalkyl, preferably a symmetrical 9-phosphabicyclo[3.3.1]nonyl group.

One or both of the phosphabicycloalkyl rings can be substituted with one or more hydrocarbyl groups containing carbon atoms and/or hetero atoms. If a phosphabicycloalkyl ring is substituted, preferably one or both of the bridges not containing the phosphorus atom is substituted, preferably with one or more alkyl groups, preferably having from 1 to 10 carbon atoms, more preferably from 1 to 4 carbon atoms. Linear, branched or cyclic alkyl groups can be used. Preferred alkyl groups include methyl, ethyl, propyl, iso-propyl, butyl and iso-butyl. More preferably methyl groups are used. The substituted phosphabicycloalkyl ring can be mono- or poly-substituted and is preferably di-substituted. Most preferably the phosphabicycloalkyl ring is substituted with two methyl groups. Examples of substituted phosphabicycloalkyl rings include 3,7 dimethyl,9-phosphabicyclo[3.3.1]nonyl; 3,7 diethyl,9-phosphabicyclo[3.3.1]nonyl; 2,6-dimethyl, 9-phosphabicyclo[3.3.1]nonyl.

Preferred bidentate diphosphines of formula II include 1,2-P,P'bis(9-phosphabicyclo[3.3.1]nonyl)ethane; 1,3-P,P'bis(9-phosphabicyclo[3.3.1]nonyl)propane; 1,2-P,P'bis(9-phosphabicyclo[3.3.1]nonyl)propane; 2,3-P,P'bis(9-phosphabicyclo[3.3.1]nonyl)butane; 2,3-P,P'bis(9-phosphabicyclo[3.3.1]nonyl)pentane; 2,4-P,P'bis(9-phosphabicyclo[3.3.1]nonyl)pentane; 1,2-P,P'bis(3,7-dimethyl, 9-phosphabicyclo[3.3.1]-nonyl)ethane; 1,3-P,P'bis(3,7-dimethyl, 9-phosphabicyclo[3.3.1]nonyl)propane; 1,2-P,P'bis(3,7-dimethyl, 9-phosphabicyclo[3.3.1]nonyl)propane; 2,3-P,P'bis(3,7-dimethyl, 9-phosphabicyclo[3.3.1]nonyl)butane; 2,3-P,P'bis(3,7-dimethyl, 9-phosphabicyclo[3.3.1]nonyl)pentane; 2,4-P,P'bis(3,7-dimethyl, 9-phosphabicyclo[3.3.1]nonyl)pentane; 1,2-P,P'bis(9-phosphabicyclo[3.3.1]nonyl)cyclopentane; 1,2-P,P'bis(9-phosphabicyclo[3.3.1]nonyl)cyclohexane; and mixtures thereof.

These bidentate diphosphines can be prepared with methods as described in WO-A-00/02375 and/or non-pre-published WO-A-01/87899.

Especially preferred are 1,2-P,P'bis(9-phosphabicyclo[3.3.1]nonyl)ethane; 1,2-P,P'bis(9-phosphabicyclo[3.3.1]nonyl)propane; and 2,3-P,P'bis(9-phosphabicyclo[3.3.1]nonyl)butane. Most preferred is 2,3-P,P'bis(9-phosphabicyclo[3.3.1]nonyl)butane.

Preferably more than 80% w/w and more preferably more than 85% w/w of the bidentate diphosphine present in the bidentate diphosphine composition of component (b) of the catalyst system has the general formula (II). Even more preferably in the range of from 90% w/w, more preferably of from 95% w/w to 100% w/w of the bidentate diphosphine present in the composition has the general formula (II). Most preferably in the range of from 99% w/w to 100% w/w of the bidentate diphosphine present in the composition has the general formula (II).

Examples of sources of Pt group metal cations of component (a) of the catalyst system are platinum or palladium compounds such as salts of palladium and nitric acid, sulphuric acid or sulphonic acids, salts of platinum or palladium and carboxylic acids with up to 12 carbon atoms, palladium or platinum complexes, e.g. with carbon monoxide or acetylacetonate, or palladium combined with a solid material such as an ion exchanger. Palladium(II) acetate and platinum(II) acetylacetonate are examples of preferred metal sources.

Some of the catalyst systems which can be used in the process according to the present invention are novel.

Accordingly, the present invention provides a catalyst system including:

(a) a source of Pt group metal cations, (b) a bidentate diphosphine composition wherein more than 60% w/w of bidentate diphosphine present in the bidentate diphosphine composition has the general formula (II)

$$X^1—R—X^2 \text{ (II)}$$

wherein $X^1$ and $X^2$ independently represent an optionally substituted symmetrical phosphabicycloalkyl group, having at least 5 ring atoms; and R represents a bivalent organic bridging group, connecting both phosphorus atoms.

Preferences for components (a) and (b) are as described hereinbefore.

Preferably the catalyst system also includes as an additional component (c) a source of anions. As anion source, any compound generating these anions can be used. Acids, or salts thereof, can be used as source of anions, for example any of the acids mentioned above, which can also participate in the salts of the metals of the platinum group.

In the process of the present invention, preferably acids are used as anion source having a pKa value of less than 6, more preferably less than 5, measured in aqueous solution at 18° C.

Typical examples of anions which can be used are anions of phosphoric acid, sulphuric acid, sulphonic acids and halogenated carboxylic acids such as trifluoroacetic acid.

Sulphonic acids are in particular preferred, for example methanesulphonic acid, trifluoromethanesulphonic acid, tert-butane-sulphonic acid, p-toluenesulphonic acid and 2,4,6-trimethylbenzene-sulphonic acid.

Also, complex anions can be used, such as the anions generated by a combination of a Lewis acid such as $BF_3$, $AlCl_3$, $SnF_2$, $Sn(CF_3SO_3)_2$, $SnCl_2$ or $GeCl_2$, with a protic acid, such as a sulphonic acid, e.g. $CF_3SO_3H$ or $CH_3SO_3H$ or a hydrohalic acid such as HF of HCl, or a combination of a Lewis acid with an alcohol. Examples of such complex anions are $BF_4^-$, $SnCl_3^-$, $[SnCl_2.CF_3SO_3]^-$ and $PF_6^-$.

The ethylenically unsaturated compound, used as starting material, is preferably an alkene having from 2 to 20 carbon atoms per molecule, or a mixture thereof. Preferred are alkenes having from 3 to 20 and more preferably from 3 to 14 carbon atoms, or mixtures thereof. They can comprise one or more double bonds per molecule but alkenes having 1 to 3 carbon-carbon double bonds per molecule are preferred. The alkene can be substituted or non-substituted. Preferred substituents include alkyl and aryl groups as well as groups containing hetero-atoms such as halides, sulphur, phosphorus, oxygen and nitrogen. Examples of substituents include chloride, bromide, iodide and hydroxy, alkoxy, carboxy, amino, amido, nitro, cyano, thiol or thioalkoxy groups. Examples of ethylenically unsaturated compounds include ethene, propene, 1-butene, 2-butene, isobutene, pentenes, hexenes, octenes and dodecenes, 1,5-cyclooctadiene, cyclododecene, methyl pentenoates and pentene nitriles.

In the process of the present invention, these ethylenically unsaturated compounds can be converted by reaction with carbon monoxide and a coreactant with a high regioselectivity towards the linear product.

In the process of the present invention, the ethylenically unsaturated starting material and the formed product can act as reaction diluent. Hence, the use of a separate solvent is not necessary. Conveniently, however, the carbonylation reaction can be carried out in the additional presence of a solvent. As such, saturated hydrocarbons, e.g. paraffins and isoalkanes, are recommended and furthermore alcohols, the saturated hydrocarbons and alcohols preferably having from 4 to 10 carbon atoms per molecule, such as butanol, ethylhexanol-1, nonanol-1, or in general terms the alcohols formed as carbonylation product; ethers such as 2,5,8-trioxanonane (diglyme), diethylether and anisole, and ketones, such as methylbutylketone. Solvents, comprising or substantially consisting of sulphones are also preferred. Sulphones are in particular preferred, for example dialkylsulphones such as dimethylsulphone and diethylsulphone and cyclic sulphones, such as sulfolane (tetrahydrothiophene-2,2-dioxide), sulfolane, 2-methylsulfolane and 2-methyl-4-ethylsulfolane.

The quantity in which the catalyst system is used is not critical and can vary within wide limits. Usually amounts in the range of $10^{-8}$ to $10^{-1}$, preferably in the range of $10^{-7}$ to $10^{-2}$ mole atom of platinum group metal per mole of ethylenically unsaturated compound are used. The amounts of the participants in the catalyst system are conveniently selected such that per mole atom of platinum group metal from 0.5 to 10, preferably from 1 to 6 moles of bidentate diphosphine are used, from 0.5 to 15, preferably from 1 to 8 moles of anion source or a complex anion source.

Furthermore the presence of a small amount of catalyst promoter comprising a source of halide anions can have a significant favourable effect in that the conversion reaction proceeds at high rate, even at moderate temperatures, with very little formation of saturated hydrocarbons.

For hydroformylation the coreactant can be molecular hydrogen, or more generally a hydride source. The carbon monoxide and hydrogen can be supplied in equimolar or non-equimolar ratios, e.g. in a ratio within the range of 5:1 to 1:5, preferably 3:1 to 1:3. More preferably they are supplied in a ratio within the range of 2:1 to 1:2.

The carbonylation can be carried out at moderate reaction conditions. Hence temperatures in the range of 50 to 200° C. are recommended, preferred temperatures being in the range of 70 to 160° C. Reaction pressures in the range of 500 to 10000 kPa (5 to 100 bar) are preferred; lower or higher pressures can be selected, but are not considered particularly advantageous. Moreover, higher pressures require special equipment provisions.

The claimed catalyst system can also be useful in conversion reactions other than hydroformylation. In general the coreactant can be represented by NuH, wherein Nu represents the remnant nucleophilic moiety of the coreactant after removal of a hydrogen atom. The nature of the coreactant largely determines the type of product formed. The coreactant can be a nucleophilic compound having a mobile hydrogen atom, such as an alcohol, an acid, an amine or water. For an alcohol XOH (X being the carbon containing part), the XO moiety is represented by Nu and accordingly the product is an ester.

Similarly, the use of an acid XCOOH (Nu=XCOO) will introduce an anhydride group in the product of the monocarbonylation reaction; the use of ammonia (Nu=NH$_2$) or an amine XNH$_2$ (Nu=XNH) or X$_2$NH (Nu=X$_2$N) will introduce an amide group; the use of a thiol XSH (Nu=XS) will introduce a thioester group; and the use of water (Nu=OH) will introduce a carboxy group.

Some of the bidentate diphosphine compositions which can be used in the process according to the present invention are novel.

Accordingly the present invention also provides a bidentate diphosphine composition wherein more than 60% w/w of bidentate diphosphine present has the general formula II

$$X^1-R-X^2 \quad (II)$$

wherein $X^1$ and $X^2$ independently represent an optionally substituted symmetrical phosphabicycloalkyl group, having at least 5 ring atoms; and R represents a bivalent organic bridging group, connecting both phosphorus atoms, with the proviso that the bidentate diphosphine is not 1,3-PP'bis(9-phosphabicyclo[3.3.1]nonyl)propane.

Preferably more than 80% w/w and more preferably more than 85% w/w of the bidentate diphosphine present in the bidentate diphosphine composition has the general formula (II). Even more preferably in the range of from 90% w/w, more preferably of from 95% w/w, to 100% w/w of the bidentate diphosphine present in the composition has the general formula (II). Most preferably in the range of from 99% w/w to 100% w/w of the bidentate diphosphine present in the composition has the general formula (II). Preferences for the bidentate diphosphine itself are as described above for the process.

Bidentate diphosphine compositions wherein a bidentate diphosphine is present having the general formula II are known in the art. For example, U.S. Pat. No. 3,527,818 describes in example I a mixture of octamethylene-PP'-bis, (9-phosphabicyclo[4.3.1]nonane), octamethylene-PP'-bis(9-phosphabicyclo[3.3.1]nonane) and octamethylene-P-(9-phosphabicyclo[4.2.1]nonane)P'(9-phosphabicyclo[3.3.1] nonane). To obtain a bidentate diphosphine composition which can be used in the process of the present invention, however, such compositions/mixtures need to be purified to obtain a higher percentage of bidentate diphosphine having the general formula (II).

The preparation of a purified bidentate diphosphine composition, that is a bidentate diphosphine composition wherein the percentage of bidentate diphosphine having the general formula (II) is as specified above, can be established as follows:

Purification of the starting compound. That is, separation of the symmetrical phosphabicycloalkane from a composition of symmetrical and asymmetrical phosphabicycloalkanes to obtain a composition with a high percentage of symmetrical phosphabicycloalkane. Bidentate diphosphines are subsequently prepared from the composition having a high percentage of symmetrical phosphabicycloalkanes. The bidentate diphosphines can be prepared as described by J. H. Downing et. al. in their article entitled "A simple procedure for the separation of the catalytically important phobane isomers" published in Chemical Communications, 1997, pages 1527–1528.

Purification of a Starting Compound.

Preferably the starting compound is purified to the extent that the resulting phosphabicycloalkane composition comprises more than 60% w/w, preferably more than 80% w/w, more preferably at least 90% w/w and even more preferably in the range of 95 to 100% w/w of symmetrical phosphabicycloalkane. Most preferably the resulting composition is essentially 100% w/w pure, that is it comprises in the range of from 99% w/w, most preferably of from 99.5% w/w to 100% w/w of symmetrical phosphabicycloalkane.

An example of the purification of a composition comprising symmetrical and asymmetrical phosphabicycloalkanes is given by J. H. Downing et al. in their article entitled "A simple procedure for the separation of the catalytically important phobane isomers", published in Chemical Communications, 1997, pages 1527–1528, which is described hereinbefore. A disadvantage of this method, however, is that it involves a number of chemical reactions, such as a reaction with formaldehyde. The use of chemical reactions slows down the process.

A novel method for the purification of a composition comprising symmetrical and asymmetrical phosphabicycloalkanes which does not involve such chemical reactions has now been found. Surprisingly it was found that symmetrical and asymmetrical phosphabicycloalkanes can be separated by exploiting a difference found in basicity between the symmetrical and asymmetrical isomer of a phosphabicycloalkane.

The present invention therefore also provides a process for the separation of symmetrical phosphabicycloalkane from a composition containing symmetrical and asymmetrical phosphabicycloalkanes comprising the following steps:

a) adding means to protonate a phosphabicycloalkane to a composition containing symmetrical phosphabicycloalkane (SPBA) and asymmetrical phosphabicycloalkane (APBA), yielding a composition comprising protonated symmetrical phosphabicycloalkane (SPBA+) and non-protonated asymmetrical phosphabicycloalkane (APBA);

b) separating protonated symmetrical phosphabicycloalkane (SPBA+) and non-protonated asymmetrical phosphabicycloalkane (APBA), yielding separated protonated symmetrical phosphabicycloalkane (SPBA+) and separated non-protonated asymmetrical phosphabicycloalkane (APBA)

c) adding means to de-protonate the separated protonated symmetrical phosphabicycloalkane (SPBA+), yielding separated non-protonated symmetrical phosphabicycloalkane (SPBA).

The novel process is faster and more easy to conduct than the process described in the article of J. Downing et al. In addition the reversibility in protonating and deprotonating the phosphabicycloalkanes make it a "forgiving" process.

By "protonate a phosphabicycloalkane" is meant that a phosphabicycloalkane accepts a proton, i.e. a positively charged hydrogen atom (H+).

Preferred means to protonate a phosphabicycloalkane include a wide range of acids, such as hydrohalic acids, e.g. hydrogen chloride, hydrogen bromide, hydrogen iodide and hydrogen fluoride; halogen oxo acids, e.g. hypobromous acid, chlorous acid, hypochlorous acid, perchloric acid and periodic acid; mineral acids, e.g. sulphuric acids, nitric acids and phosphoric acids; some organic acids, such as acetylacetonic acids, sulphonic acids, carboxylic acids and halogenated carboxylic acids e.g. trichloroacetic acid and trifluoroacetic acid; complex acids such as $HBF_4$, $HSnCl_3$; and mixtures of those acids.

More preferred are inorganic acids such as the hydrohalic acids, halogen oxo acids and mineral acids mentioned. More preferred are hydrohalic acids of which HCl, HI, and HBr are most preferred.

Preferred means to de-protonate the separated protonated symmetrical phosphabicycloalkane (SPBA+) in step c) include a wide range of bases, such as ammonia and primary, secondary and tertiary amines; carbonates and hydrogencarbonates, such as for example $Na_2CO_3$, $NaHCO_3$, $K_2CO_3$, $MgCO_3$; and hydroxides such as $Ba(OH)_2$, $Na(OH)$ and $K(OH)$. More preferred are alkali metal hydroxides, such as potassium hydroxide and sodium hydroxide.

Preferably the separation in step b) is achieved by making use of a difference in solubility of SPBA+ and APBA. Preferably a composition containing SPBA and APBA is solved in a solvent which does not dissolve SPBA+. Means to protonate a phosphabicycloalkane, such as for example a hydrohalogenic acid, can be added to the dissolved phosphabicycloalkanes as a gas, as a (dissolved) liquid or a solid, whichever is most suitable. For example a HCl gas or a 1 M aqueous solution of HCl can be added to a diethylether solution of phoshabicycloalkanes. The SPBA+ can subsequently be separated as a precipitated solid or as a solution in a second liquid phase. The precipitate can, however, be thick and sticky and difficult to handle in isolation and purification.

Preferably the separation in step b) is therefore achieved by phase separation. An especially preferred process for the separation of symmetrical phosphabicycloalkane from a composition containing symmetrical and asymmetrical phosphabicycloalkanes accordingly comprises:

i] dissolving a composition containing SPBA and APBA in a suitable non-water miscible solvent, which does not dissolve SPBA+, yielding a non-aqueous phosphabicycloalkane (PBA) solution;

ii] combining the non-aqueous PBA solution with an aqueous solution of a suitable acid, yielding an aqueous phase containing protonated SPBA+ and a non-aqueous phase containing non-protonated APBA;

iii] separating the aqueous phase containing protonated SPBA+ and the non-aqueous phase containing non-protonated APBA, yielding an aqueous solution containing protonated SPBA+ and a non-aqueous solution containing non-protonated APBA;

iv] combining the aqueous solution containing protonated SPBA+ with a suitable non-water miscible solvent and an aqueous solution of a suitable base, yielding a non-aqueous solution containing non-protonated SPBA;

v] removing the solvent from the non-aqueous solution containing non-protonated SPBA, yielding separated SPBA.

Optionally an extra step vi] is added to the process comprising removing the solvent from the non-aqueous solution containing non-protonated APBA, yielding separated APBA.

By a non-water miscible solvent is meant a hydrophobic solvent. Such a solvent can be mixed with water but upon standing two phases will eventually separate.

A wide range of non-water miscible solvents are available in which SPBA and APBA can be solved and which do not dissolve SPBA+. By not dissolving SPBA+ is understood that this compound is essentially not dissolved, that is the molar ratio SPBA+ dissolved in the solvent to SPBA+ dissolved in an aqueous 6 M HCl solution lies in the range from 10:90 to 0:100 and more preferably in the range from 5:95 to 0:100.

Preferably the solvent is an aprotic solvent. Solvents which can be used include saturated and unsaturated hydrocarbons, e.g. paraffins and linear, branched and cyclic alkanes, alkenes and alkynes, such as hexane, hexene, pentene and pentane, aromatics such as toluene and benzene; ethers, such as for example dimethylether anisole (methyl phenyl ether), 2,5,8-trioxanonane (diglyme), diethylether, tetrahydrofuran, diphenylether, diisopropylether and the dimethylether of di-ethyleneglycol; esters, such as for example methylacetate, dimethyladipate, butyrolactone, propionates and pentenoates; ketones, such as methylbutylketone and diethylketone; and sulphones, for example dialkylsulphones such as dimethylsulphone and diethylsulphone and cyclic sulphones, such as sulfolane (tetrahydrothiophene-2,2-dioxide), 2-methylsulfolane and 2-methyl-4-ethylsulfolane.

Preferred are aprotic solvents having a dielectric constant that is below a value of 50, more preferably in the range of 1 to 8, at 298.15° K and 100 kPa (1 bar). In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et al, and published by CRC press in 1995, and are usually quoted for a temperature of about 20 or 25° C., i.e. about 293.15 or 298.15° K, and atmospheric pressure, i.e. about 100 kPa (1 bar), or can readily be converted to that temperature and pressure using the conversion factors quoted. If no literature data for a particular compound is available, the dielectric constant can be readily measured using established physico-chemical methods.

For example, the dielectric constant of anisole is 4.3 (at 294.2° K), of diethyl ether is 4.3 (at 293.2° K), of sulfolane is 43.4 (at 303.2° K), of diphenylether is 3.7 (at 283.2° K), of dimethyladipate is 6.8 (at 293.2° K), of tetrahydrofuran is 7.5 (at 295.2° K), of methylnonanoate is 3.9 (at 293.2° K), of toluene is 2.4 (at 296.4° K), of pentane is 1.8 (at 293.2° K).

Most preferred solvents are saturated alkanes and aromatics, such as hexane, pentane or toluene and ethers. Ethers are especially preferred because the use of ethers in this separation process results in a quick and efficient phase-separation. Examples of ethers which can be used include dimethylether, methylethylether, anisole, diethylether and diphenylether.

Another especially preferred solvent is toluene, since toluene is less volatile and less flamable than some of the other solvents and therefore easy to handle. In addition a phosphabicycloalkane composition is conveniently supplied as a toluene solution.

The concentrations of the reactants can be varied over a wide range, but is preferably kept high so as to reduce the amounts of solvent to be used. Phosphabicycloalkanes are preferably dissolved in the non-water miscible solvent to give a concentration in the range of 0.01 to 10 molar, more preferably in the range from 0.1 to 5 molar.

Preferred acids in step ii] are as described above for means to protonate a phosphabicycloalkane. Preferably concentrations in the range from 2 to 20 molar are used, and more preferably concentrations in the range from 5 to 15 molar are used. Most preferred are concentrations in the range from 5 to 10 molar.

The aqueous solution of suitable acid in step ii] can be added as such to the non-aqueous PBA solution or can be prepared in situ by first adding water and subsequently adding acid in a more concentrated form.

Preferably a ratio of aqueous solution to non-aqueous solution in step ii] is used in the range from 1:10 to 10:1 v/v, more preferably in the range from 1:2 to 2:1 v/v.

After combining the non-aqueous PBA solution with a aqueous solution of suitable acid the system is preferably shaken or stirred, such to establish close contact between the acid and the phosphabicycloalkanes, whereafter the two phases are allowed to separate. The two phases are separated in step iii]. Preferably the aqueous solution containing protonated SPBA+ is extracted one or more, preferably in the range from 1 to 50, times with a non-water miscible solvent as described for step i] to remove residues of non-protonated phosphabicycloalkanes and protonated APBA+.

Similarly the non-aqueous solution containing non-protonated APBA is preferably extracted one or more, preferably in the range from 1 to 50, times with a aqueous solution of a suitable acid to remove residues of protonated SPBA+.

Subsequently the aqueous solution containing protonated SPBA+ is combined in step iv] with a non-water miscible solvent as described for step i] and an aqueous solution of a suitable base, yielding a non-aqueous solution containing non-protonated SPBA;

Preferred bases are as described above for means to de-protonate the protonated symmetrical phosphabicycloalkane. Preferably concentrations in the range from 2 to 20 molar are used, and more preferably concentrations in the range from 5 to 15 molar are used.

Optionally residues of water are removed from the non-aqueous solutions yielded in steps iii] and/or iv] in a way known to one skilled in the art. For example residues of water can be removed by washing with bases such as hydroxides and carbonates, such as $Na_2CO_3$, $NaHCO_3$, $K_2CO_3$, $MgCO_3$, $Ba(OH)_2$, Na (OH) and K(OH). Subsequently a non-aqueous solution can be dried over a drying agent such as for example $K_2SO_4$, $Na_2SO_4$ and $MgSO_4$.

Removal of the non-aqueous solvents in steps v] and vi] can be established in any way known to one skilled in the art to remove such solvents.

Further purification can be be established by sublimation of the isomers. Preferably pressures in the range from 0.0033 to 0.33 kPa (0.025 to 2.5 mm Hg), more preferably in the range from 0.027 to 0.27 kPa (0.2 to 2 mm Hg) are used. Depending on the pressure applied, the temperatures can vary widely. Preferably a temperature in the range of 40° C. and higher is used, more preferably a temperature in the range from 40° C. to 90° C. is used.

The present invention will be illustrated by the following non-limiting examples.

EXAMPLE 1

The experiment was carried out in a 250 ml magnetically stirred Hastelloy C autoclave (Hastelloy is a trademark). The autoclave was charged with 10 ml of propene, 40 ml anisole and 10 ml sulfolane, 0.25 mmol of platinum(II) acetylacetonate, 0.3 mmol of 1,2-PP'bis(9-phosphabicyclo[3.3.1]nonyl)ethane with a purity of >99%, 0.3 mmol $SnCl_2$ and 0.3 mmol HCl. After being flushed, the autoclave was pressurised with carbon monoxide and hydrogen to a partial pressure of 3000 kPa (30 bar) of each. Subsequently, the reactor was sealed and the contents were heated to 115° C. and maintained at that temperature for 1.5 hours. After cooling, a sample was taken from the contents of the reactor and analysed by Gas Liquid Chromatography. The selectivity towards the linear product n-butyraldehyde was 98.6%.

EXAMPLE 2

The experiment was carried out in a 250 ml magnetically stirred Hastelloy C autoclave. The autoclave was charged with 10 ml of propene, 40 ml anisole and 10 ml sulfolane, 0.25 mmol of platinum(II) acetylacetonate, 0.3 mmol of 1,3-PP'bis(9-phosphabicyclo[3.3.1]nonyl)-propane with a purity of >99%, 0.3 mmol $SnCl_2$ and 0.3 mmol HCl. After being flushed, the autoclave was pressurised with carbon monoxide and hydrogen to a partial pressure of 3000 kPa (30 bar) of each. Subsequently, the reactor was sealed and the contents were heated to 115° C. and maintained at that temperature for 1.5 hours. After cooling, a sample was taken from the contents of the reactor and analysed by Gas Liquid Chromatography. The selectivity towards the linear product n-butyraldehyde was 90.8%.

EXAMPLE 3

The example was carried out in a 250 ml magnetically stirred Hastelloy C autoclave. The autoclave was charged with 10 ml of propene, 40 ml anisole and 10 ml sulfolane, 0.25 mmol of platinum(TI) acetylacetonate, 0.3 mmol of meso (R,S) 2,3-PP'bis(9-phosphabicyclo[3.3.1]nonyl)butane with a purity of >99% by weight, 0.3 mmol $SnCl_2$ and 0.3 mmol HCl. After being flushed, the autoclave was pressurised with carbon monoxide and hydrogen to a partial pressure of 3000 kPa (30 bar) of each. Subsequently, the reactor was sealed and the contents were heated to 100° C. and maintained at that temperature until the reaction was substantially complete. Complete propene conversion occurred in 0.5 hr. After cooling, a sample was taken from the contents of the reactor and analysed by Gas Liquid Chromatography. The selectivity towards the linear product n-butyraldehyde was 99.0%.

EXAMPLE 4

Separation of Phosphabicyclononanes

A mixture of symmetrical and asymmetrical phosphabicyclononanes (33.9 g, 239 mmol, 153 mmol symmetrical: 86 mmol asymmetrical isomer) was dissolved in diethyl ether (240 ml). Subsequently deoxygenated water (240 ml) was added. The biphasic mixture was stirred vigorously while deoxygenated concentrated HCl solution (240 ml, 6 molar) was added over 90 min. The two phases were then separated and the aqueous phase was extracted 20 times with diethyl ether (50 ml each). The organic phases were combined (to reduce the volume, some of the solvent can be removed in vacuum before continuing the work-up) and washed with a concentrated HCl solution (2 ml), and subsequently washed with a saturated $NaHCO_3$ solution (30 ml). Hereafter the organic solution was dried over $MgSO_4$ and filtered over basic alumina. The solvent was removed in vacuum to give the asymmetrical isomer in a yield of 9.52 g (equivalent to 67.1 mmol, about 78% of amount of asymmetrical isomer started with) in a 100% purity as a colourless solid. To the vigorously stirred aqueous phase fresh diethyl ether (200 ml) was added, the mixture was cooled to 0° C. and a 14.4 M NaOH solution (200 ml) was added over 1.5 h. The phases were separated and the aqueous phase was washed four times with diethyl ether (50 ml each). The combined organic phases were dried over $MgSO_4$ and filtered over basic alumina. The solvent was removed in vacuum to give the symmetrical isomer in a yield of 19.79 g (equivalent to 139 mmol, about 91% of amount of asymmetrical isomer started with) in a 90% purity. Sublimation of the 90% pure symmetrical isomer at 0.27 kPa (2 mm Hg) and 60° C. gave a sample of 98% pure symmetrical isomer in 80% recovery (15.83 g, 111 mmol) as a colourless solid.

We claim:

1. A process for the separation of symmetrical phosphabicycloalkane from a composition containing symmetrical and asymmetrical phosphabicycloalkanes comprising:
   a) adding a source to protonate said composition containing symmetrical phosphabicycloalkane (SPBA) and asymmetrical phosphabicycloalkane (APSA), thereby providing a composition comprising protonated symmetrical phosphabicycloalkane (SPBA+) and non-protonated asymmetrical phosphabicycloalkane (APBA); wherein said source to protonate is an acid;
   b) separating protonated symmetrical phosphabicycloalkane (SPBA+) and non-protonated asymmetrical phosphabicycloalkane (APSA), thereby providing separated protonated symmetrical phosphabicycloalkane (SPBA+) and separated non-protonated asymmetrical phosphabicycloalkane (APBA); and
   c) adding a source to de-protonate the separated protonated symmetrical phosphabicycloalkane (SPBA+), thereby providing separated symmetrical phosphabicycloalkane (SPBA); wherein said source to de-protonate is a base.

2. The process of claim 1 wherein the separation of symmetrical phosphabicycloalkane (SPBA+) in step b) comprises the steps of:
   i) dissolving the composition comprising symmetrical phosphabicycloalkane (SPBA+) and non-protonated asymmetrical phosphabicycloalkane (APBA) in a non-water miscible solvent, which does not dissolve protonated symmetrical phosphabicycloalkane (SPBA+), thereby providing a non-aqueous phosphabicycloalkane (PBA) solution;
   ii) combining the non-aqueous PBA solution with an aqueous solution of an acid, thereby providing an aqueous phase containing SPBA+ and a non-aqueous phase containing APBA;
   iii) separating the aqueous phase containing SPBA+ and the non-aqueous phase containing APBA, thereby providing an aqueous solution containing SPBA+ and a non-aqueous solution containing APBA;

and step c) comprises the steps of:
   iv) combining the aqueous solution containing SPBA+ with a non-water miscible solvent and an aqueous solution of said base, thereby providing a non-aqueous solution containing SPBA; and
   v) removing the non-water miscible solvent from the non-aqueous solution containing SPBA, thereby producing separated SPBA.

3. The process of claim 1 further comprising step d) wherein the non-water miscible solvent is removed from the non-aqueous solution containing APBA, thereby providing separated APBA.

4. The process of claim 1 wherein the acid is selected from the group consisting of halogen oxo acids, acetylacetonic acids, sulfonic acids, carboxylic acids, halogenated carboxylic acids, mineral acids, $HBF_4$, $HSnCl_3$, and mixtures of those acids.

5. The process of claim 4 wherein the acid is selected from the group consisting of hydrochloric acid, hydrobromic acid, hydroiodic acid, hydrofluoric acid, hypobromous acid, chlorous acid, hypochlorous acid, perchloric acid, periodic acid, sulfuric acids, nitric acids, phosphoric acids, trichloroacetic acid, trifluoroacetic acid, $HBF_4$, $HSnCl_3$, and mixtures of those acids.

6. The process of claim 5 wherein the acid is selected from the group consisting of hydrochloric acid, hydrobromic acid, and hydroiodic acid.

7. The process of claim 1 wherein the base is selected from the group consisting of ammonia, primary amines, secondary amines, tertiary amines, carbonates, hydrogen carbonates, and hydroxides.

8. The process of claim 7 wherein the base is selected from the group consisting of ammonia, sodium carbonate, sodium bicarbonate, potassium carbonate, magnesium carbonate, barium hydroxide, sodium hydroxide, and potassium hydroxide.

9. The process of claim 8 wherein the base is selected from the group consisting of potassium hydroxide and sodium hydroxide.

* * * * *